(12) United States Patent
Li et al.

(10) Patent No.: US 11,286,511 B2
(45) Date of Patent: Mar. 29, 2022

(54) METHOD FOR PREPARING TROXERUTIN ESTER USING WHOLE-CELL CATALYSIS

(71) Applicant: SOUTH CHINA UNIVERSITY OF TECHNOLOGY, Guangdong (CN)

(72) Inventors: Xiaofeng Li, Guangdong (CN); Xuan Xin, Guangdong (CN); Guanglei Zhao, Guangdong (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 121 days.

(21) Appl. No.: 16/617,503

(22) PCT Filed: Nov. 30, 2017

(86) PCT No.: PCT/CN2017/113808
§ 371 (c)(1),
(2) Date: Nov. 27, 2019

(87) PCT Pub. No.: WO2018/218903
PCT Pub. Date: Dec. 6, 2018

(65) Prior Publication Data
US 2020/0181668 A1 Jun. 11, 2020

(30) Foreign Application Priority Data

May 27, 2017 (CN) .......................... 201710392731.9

(51) Int. Cl.
*C12P 19/60* (2006.01)
*C12N 1/20* (2006.01)

(52) U.S. Cl.
CPC ................ *C12P 19/60* (2013.01); *C12N 1/20* (2013.01)

(58) Field of Classification Search
None
See application file for complete search history.

(56) References Cited

U.S. PATENT DOCUMENTS

2007/0184098 A1    8/2007   Moussou et al.

FOREIGN PATENT DOCUMENTS

| CN | 101704866 | 5/2010 |
|---|---|---|
| CN | 102718818 | 10/2012 |
| CN | 104726375 | 6/2015 |
| CN | 105002238 | 10/2015 |
| CN | 105063137 | 11/2015 |
| CN | 107163096 A | * 9/2017 |
| CN | 107164423 | 9/2017 |

OTHER PUBLICATIONS

Prather, K., "Lecture #5—Using Whole Cells as Biocatalysts: Why/When, Growth vs Conversion (Screening)", 5 pages, 2004 (Year: 2004).*
Xin et al., "Biocatalytic synthesis of acylated derivatives oftroxerutin: their bioavailability and antioxidant properties in vitro", Microb. Cell Fact. 17:130, Aug. 2018, 11 pages (Year: 2018).*
Translation of Lai, X. ("Whole Cell Mediated Acylation of Esculin and Naringin", Thesis of Master Degree, South China University of Technology, Dec. 2015, pp. 1-89), 55 pages (Year: 2021).*
Translation of CN 107163096 A, obtained from Google Patents, 13 pages (Year: 2021).*
Translation of CN 107164423 A, obtained from Google Patents, 10 pages (Year: 2021).*
Xuan Xin et al., "Facile and Efficient Acylation of Bioflavonoids Using Whole-Cell Biocatalysts in Organic Solvents", ACS Sustainable Chemistry & Engineering, vol. 5, Oct. 11, 2017, pp. 10662-10672.
Xueneng Lai,"Whole Cell Mediated Acylation of Esculin and Naringin", Thesis of Master Degree, South China University of Technology, Dec. 15, 2015, pp. 1-89.
Xiao, Yongmei et al., "Enzymatic Synthesis of Vinyl Troxerutin Esters in Nonaqueous Medium", Chinese Journal of Organic Chemistry, vol. 30, No. 4, Apr. 2010, with English abstract, pp. 551-557.
Yong Mei Xiao et al., "Regioselective enzymatic acylation of troxerutin in nonaqueous medium", Chinese Chemical Letters, vol. 21, Dec. 2010, pp. 59-62.
"International Search Report (Form PCT/ISA/210) of PCT/CN2017/113808," dated Jan. 24, 2018, with English translation thereof, pp. 1-6.

* cited by examiner

*Primary Examiner* — David Steadman
(74) *Attorney, Agent, or Firm* — JCIPRNET

(57) ABSTRACT

A method for preparing troxerutin ester using whole-cell catalysis belongs to the fields of biological catalysis and pharmaceutical chemistry. The method specifically includes the following steps: evenly mixing troxerutin and a mixed organic solvent containing pyridine, then adding an acyl donor and a whole-cell catalyst, and performing a reaction under oscillation at a reaction temperature of 25° C. to 55° C.; and after the reaction is finished, separating and purifying a product by column chromatography or thin-layer chromatography, so as to obtain the troxerutin ester. The invention has the advantages of mild reaction conditions, environmental friendliness, simple process, fewer side reactions and high selectivity.

7 Claims, 3 Drawing Sheets

METHOD FOR PREPARING TROXERUTIN ESTER USING WHOLE-CELL CATALYSIS

CROSS-REFERENCE TO RELATED APPLICATION

This application is a 371 application of international PCT application Ser. No. PCT/CN2017/113808, filed on Nov. 30, 2017, which claims the priority benefit of Chinese application no. 201710392731.9, filed on May 27, 2017. The entirety of each of the above-mentioned patent applications is hereby incorporated by reference herein and made a part of this specification.

BACKGROUND

Technical Field

The present invention belongs to the field of biological catalysis and pharmaceutical chemistry, and particularly relates to a method for preparing troxerutin ester using whole-cell catalysis.

Description of Related Art

Flavonoids are a kind of important natural polyhydroxy compounds, which have many physiological functions such as oxidative stability, anticancer, antibacterial, etc. Troxerutin belongs to a kind of the flavonoids, and is widely found in tea, coffee beans, grains and various fruits and vegetables. In addition, the troxerutin may also be derived from rutin. The troxerutin has many pharmacological and physiological activities such as analgesia, inhibition of agglutination of erythrocytes and platelets, prevention of cerebral thrombosis, anti-bacteria and anti-inflammation, elimination of free radicals and treatment of diabetes. It is widely used in the treatment of cardiovascular diseases, diabetes mellitus and cerebrovascular diseases. However, due to the structure limit, the troxerutin has a poor liposolubility, thus reducing a bioavailability thereof and greatly affecting the development and application of the troxerutin.

At present, the research progresses on enhancing the liposolubility of the troxerutin mainly include: synthesizing troxerutin ester by chemical and enzymatic methods and modifying a formulation of the troxerutin to prepare a W/O microemulsion. However, the synthesis of the troxerutin ester by the chemical method is mainly to catalyze with strong acid or alkali, and the large use of acid and alkali catalysts leads to serious environmental pollution problems. Moreover, the chemical synthesis has the disadvantages of poor regioselectivity, many by-products, low yield, etc. Although the bioavailability of the troxerutin can be improved to some extent by modifying the formulation of the troxerutin, the preparation of the microemulsion requires a large amount of surfactant, and these surfactants (such as lecithin) are expensive, resulting in high production cost. Moreover, reports show that the toxicity of the surfactant is increased with the increased dosage of the surfactant. The enzymatic method has a strong specificity, but free enzymes are tedious and complicated to separate and purify, and are easily affected by an extreme reaction environment, while commercial enzymes are expensive, which are not conducive to industrial application.

In addition to the enzyme catalysis, the biological catalysis also includes whole-cell catalysis, which refers to a process of performing chemical conversion using complete microbial whole cells as a catalyst, in which an enzyme system in the microbial whole cells plays a catalytic role. Compared with the enzyme catalysis technology, the whole-cell catalyst is simple and easy to prepare, and complicated enzyme separation, purification and immobilization processes may be omitted, thus reducing the production cost. Moreover, the whole cell has a complete cell structure and cell membrane, and the enzyme is protected in the cell in a natural immobilization mode, thus being beneficial for maintaining conformation and catalytic activity of the enzyme to the greatest extent in reaction environments such as organic solvent, extreme pH, high temperature and the like. Moreover the whole cell can provide different enzyme systems and cofactors for multi-step biotransformation reactions, and can effectively realize coenzyme regeneration. The whole-cell catalysis technology has also been increasingly applied to the research on the catalytic preparation of flavone ester. However, the research on the preparation of the troxerutin ester using the whole-cell catalysis has not been reported.

SUMMARY

An object of the present invention is to overcome the defects in the prior art and provide a green, simple and efficient method for preparing troxerutin ester using whole-cell catalysis.

The object of the present invention is achieved by the following technical solutions.

A method for preparing troxerutin ester using whole-cell catalysis includes the following steps:

(1) evenly mixing a mixed organic solvent containing pyridine, with troxerutin, then adding an acyl donor, and adding microbial cells as a catalyst for a reaction under oscillation; and (2) after the reaction is finished, separating and purifying a reaction liquid to obtain troxerutin ester.

Preferably, the mixed organic solvent containing pyridine in the step (1) is a binary mixed solvent composed of pyridine and one of dimethyl sulfoxide, N,N-dimethylformamide, acetonitrile, tetrahydrofuran, tert-butyl alcohol, tert-amyl alcohol, cyclohexane, n-hexane, petroleum ether, n-heptane and isooctane.

Further preferably, a volume content of the pyridine in the mixed organic solvent ranges from 25% to 90%.

Preferably, the acyl donor in the step (1) is fatty acid with 1 to 18 carbon atoms, fatty acid ester with 1 to 18 carbon atoms, or fatty acid enol ester.

Preferably, a molar ratio of the troxerutin to the acyl donor in the step (1) is 1:5 to 1:40, and is further preferably 1:10-1:40.

Preferably, the microbial cell in the step (1) is *Pseudomonas stutzeri, Pseudomonas cepacia, Pseudomonas putida, Pseudomonas fluorescens, Pseudomonas aeruginosa, Bacillus subtilis, Bacillus megaterium, Rhizopus oligosporus, Aspergillus niger, Penicillium citrinum, Rhizopus chinensis, Rhizomucor miehei, Rhizopus oryzae, Aspergillus oryzae* or *Geotrichum candidum*.

Preferably, a mass ratio of the microbial cell to the troxerutin in the step (1) is 2:3 to 8:3.

Preferably, a dosage of the microbial cells in the step (1) is 20 mg/mL to 80 mg/mL.

Preferably, a temperature of the reaction in the step (1) ranges from 20° C. to 55° C.

Preferably, the reaction in the step (1) lasts for 24 hours to 156 hours.

Preferably, the separating and purifying in the step (2) includes centrifuging the reaction liquid after the reaction to remove thallus, then performing reduced pressure distillation to remove the solvent, and separating by column chromatography or thin-layer chromatography to obtain the troxerutin ester; and a chromatography liquid used is ethyl acetate/methanol/water with a volume ratio of 15:3.6:0.5.

Compared with the prior art, the present invention has the following advantages.

(1) In the present invention, efficient biocatalyst-microbial cells are adopted to catalyze and prepare the troxerutin ester. As the whole-cell catalyst has a complete cell structure, and a cell ligase therein is protected in the whole cell in a natural immobilization mode, so that the defects of easy inactivation of free enzymes and low reaction yield in an extreme reaction environment in the prior art are overcome.

(2) The present invention does not need radical protection and deprotection operation, and the reaction process is simple and easy to control.

(3) The whole-cell catalyst needed by the reaction is simple to prepare, easy to obtain and is cheap, thus avoiding the complicated separating and purifying process of the free enzymes and the high production cost of commercial enzymes.

(4) According to the present invention, the thallus can be recovered through simple filtration after the reaction is finished, so that the whole-cell catalyst is repeatedly utilized, and the product is easy to be separated and purified.

(5) The present invention has the advantages of mild reaction conditions, environmental friendliness, simple process, fewer side reactions and high selectivity.

DESCRIPTION OF THE EMBODIMENTS

In order to better understand the present invention, the present invention will be described in further detail below with reference to the embodiments, but the scope of protection claimed by the present invention is not limited to the scope represented in the embodiments.

Embodiment 1

Figure 1:
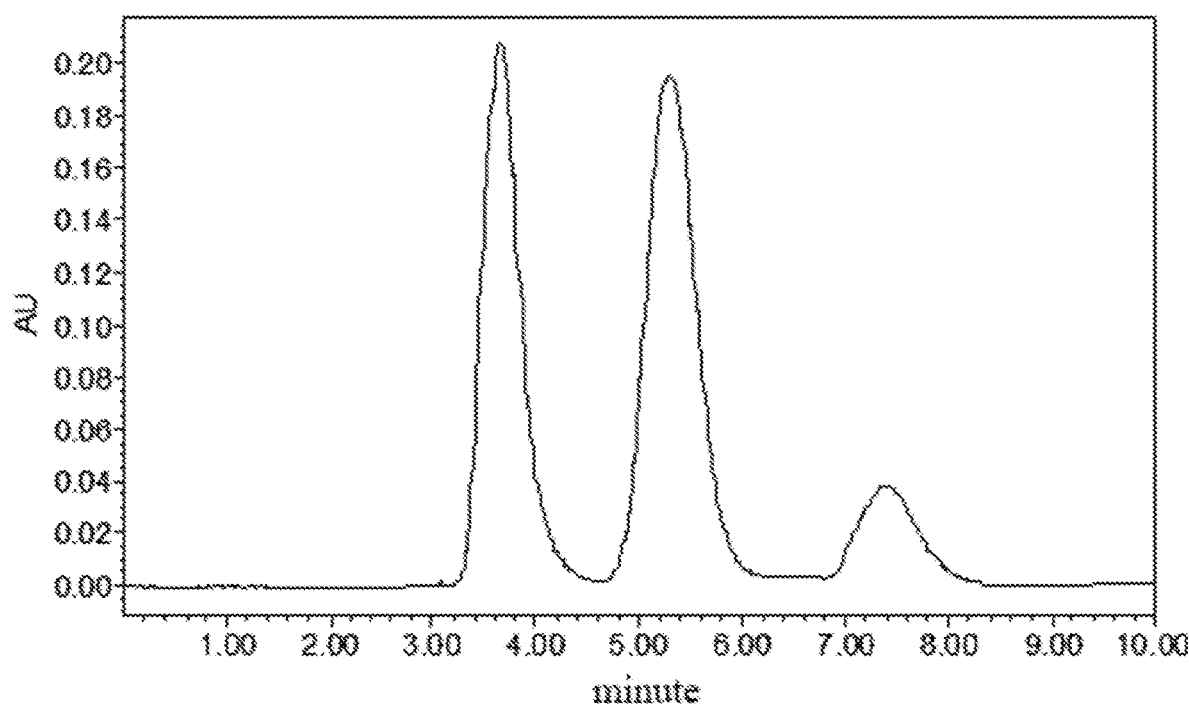
FIG. 1 is a high performance liquid chromatogram of a synthesis process of troxerutin ester.
Figure 2:
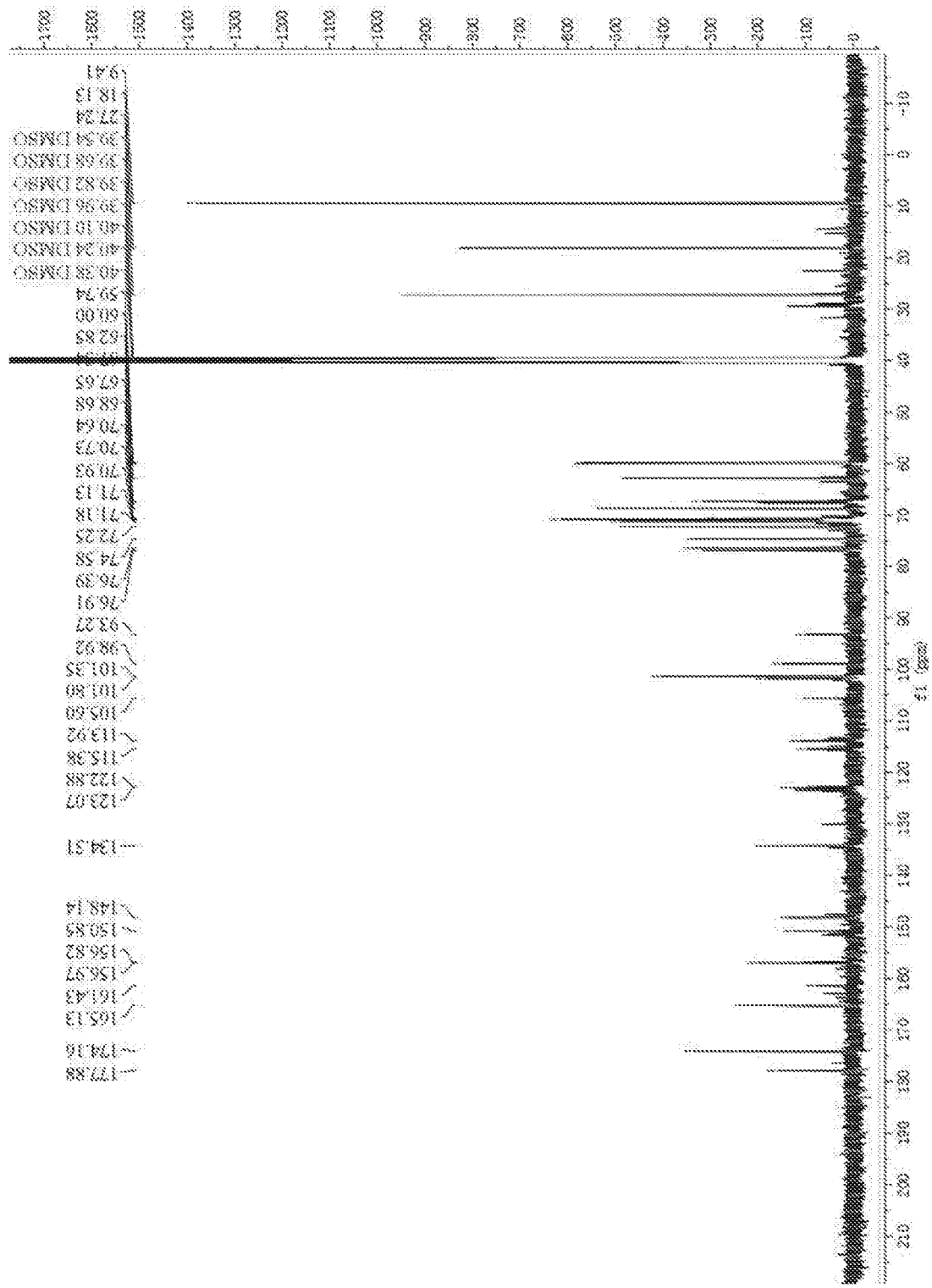
FIG. 2 is a nuclear magnetic resonance carbon spectrum of troxerutin monoester.

30 mmol of troxerutin was dissolved in 1 mL of pyridine-isooctane mixed organic solvent (a volume content of the pyridine was 25%), then added with vinyl propionate (a molar ratio of the troxerutin to the vinyl propionate was 1:20) and mixed evenly, and then *Pseudomonas aeruginosa* GIM1.46 (Guangdong Institute of Microbiology) (a mass ratio of the *Pseudomonas aeruginosa* to the troxerutin was 2:1), and reacted for 24 hours at 20° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester, wherein a high performance liquid chromatogram of the synthesis process was shown in FIG. 1. A chromatography liquid used was ethyl acetate/methanol/water with a volume ratio of 15:3.6:0.5. Under the implementation conditions, a substrate transformation ratio was 12% and a yield of troxerutin monoester was 10.1%. A nuclear magnetic resonance carbon spectrum of the troxerutin monoester is as shown in FIG. 2.

Embodiment 2

Figure 3:
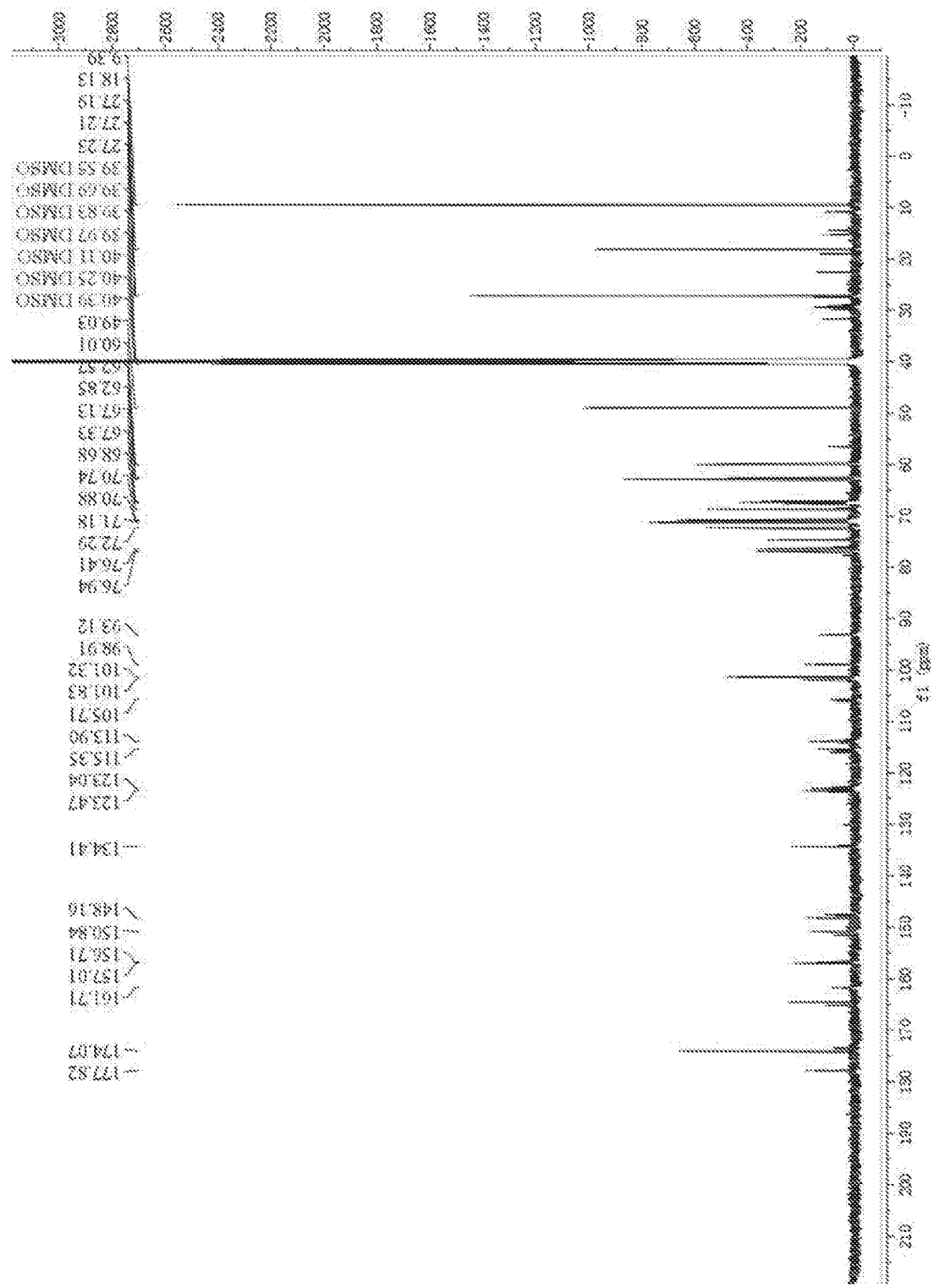
FIG. 3 is a nuclear magnetic resonance carbon spectrum of troxerutin diester.

30 mmol of troxerutin was dissolved in 1 mL of pyridine-isooctane mixed organic solvent (a volume content of the pyridine was 25%), then added with vinyl propionate (a molar ratio of the troxerutin to the vinyl propionate was 1:20) and mixed evenly, and then *Pseudomonas stutzeri* GIM1.273 (Guangdong Institute of Microbiology) (a mass ratio of the *Pseudomonas stutzeri* to the troxerutin was 2:1), and reacted for 90 hours at 37.5° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 78.2% and a yield of troxerutin diester was 60.2%. A nuclear magnetic resonance carbon spectrum of the troxerutin diester is as shown in FIG. 3.

Embodiment 3

30 mmol of troxerutin was dissolved in 1 mL of pyridine-n-heptane mixed organic solvent (a volume content of the pyridine was 25%), then added with vinyl propionate (a molar ratio of the troxerutin to the vinyl propionate was 1:20) and mixed evenly, and then *Pseudomonas aeruginosa* GIM1.46 (a mass ratio of the *Pseudomonas aeruginosa* to the troxerutin was 2:1), and reacted for 156 hours at 55° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 80.1% and a yield of troxerutin monoester was 72%.

Embodiment 4

30 mmol of troxerutin was dissolved in 1 mL of pyridine-n-heptane mixed organic solvent (a volume content of the pyridine was 90%), then added with vinyl propionate (a molar ratio of the troxerutin to the vinyl propionate was 1:20) and mixed evenly, and then *Pseudomonas aeruginosa* GIM1.46 (a mass ratio of the *Pseudomonas aeruginosa* to the troxerutin was 2:1), and reacted for 48 hours at 40° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 34.4% and a yield of troxerutin monoester was 27.7%.

Embodiment 5

30 mmol of troxerutin was dissolved in 1 mL of pyridine-n-heptane mixed organic solvent (a volume content of the pyridine was 65%), then added with vinyl propionate (a molar ratio of the troxerutin to the vinyl propionate was 1:10) and mixed evenly, and then *Pseudomonas aeruginosa* GIM1.46 (a mass ratio of the *Pseudomonas aeruginosa* to the troxerutin was 2:1), and reacted for 120 hours at 40° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 60.1% and a yield of troxerutin monoester was 44.7%.

Embodiment 6

30 mmol of troxerutin was dissolved in 1 mL of pyridine-n-heptane mixed organic solvent (a volume content of the pyridine was 65%), then added with vinyl propionate (a molar ratio of the troxerutin to the vinyl propionate was 1:40) and mixed evenly, and then *Pseudomonas aeruginosa* GIM1.46 (a mass ratio of the *Pseudomonas aeruginosa* to the troxerutin was 2:1), and reacted for 120 hours at 40° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 89.4% and a yield of troxerutin monoester was 78.5%.

Embodiment 7

30 mmol of troxerutin was dissolved in 1 mL of pyridine-n-heptane mixed organic solvent (a volume content of the pyridine was 65%), then added with vinyl propionate (a molar ratio of the troxerutin to the vinyl propionate was 1:30) and mixed evenly, and then *Pseudomonas aeruginosa* GIM1.46 (a mass ratio of the *Pseudomonas aeruginosa* to the troxerutin was 1:1), and reacted for 120 hours at 40° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 65.7% and a yield of troxerutin monoester was 50%.

Embodiment 8

30 mmol of troxerutin was dissolved in 1 mL of pyridine-n-heptane mixed organic solvent (a volume content of the pyridine was 65%), then added with vinyl propionate (a molar ratio of the troxerutin to the vinyl propionate was 1:30) and mixed evenly, and then *Pseudomonas aeruginosa* GIM1.46 (a mass ratio of the *Pseudomonas aeruginosa* to the troxerutin was 4:1), and reacted for 120 hours at 40° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 96.2% and a yield of troxerutin monoester was 81.2%.

Embodiment 9

30 mmol of troxerutin was dissolved in 1 mL of pyridine-n-heptane mixed organic solvent (a volume content of the pyridine was 65%), then added with vinyl propionate (a molar ratio of the troxerutin to the vinyl propionate was 1:30) and mixed evenly, and then *Pseudomonas aeruginosa* GIM1.46 (a mass ratio of the *Pseudomonas aeruginosa* to the troxerutin was 5:2), and reacted for 120 hours at 25° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 40.4% and a yield of troxerutin monoester was 34.6%.

Embodiment 10

30 mmol of troxerutin was dissolved in 1 mL of pyridine-n-heptane mixed organic solvent (a volume content of the pyridine was 65%), then added with vinyl propionate (a molar ratio of the troxerutin to the vinyl propionate was 1:30) and mixed evenly, and then *Pseudomonas aeruginosa* GIM1.46 (a mass ratio of the *Pseudomonas aeruginosa* to the troxerutin was 5:2), and reacted for 120 hours at 55° C. and at an oscillation speed of 180 r/min. After the reaction was finished, a reaction mixture was subjected to centrifugation to remove thallus, then reduced pressure distillation to remove the solvent, and separation by thin-layer chromatography to obtain troxerutin ester. A chromatography liquid used was ethyl acetate/methanol/water with a volume ratio of 15:3.6:0.5. Under the implementation conditions, a substrate transformation ratio was 63.4% and a yield of troxerutin monoester was 53.5%.

The above-mentioned embodiments of the present invention are merely examples for clearly illustrating the present invention, but are not intended to limit the embodiments of the present invention. For those of ordinary skills in the art, other different forms of changes or variations can be made on the basis of the above description. It is not necessary or possible to exhaust all the embodiments here. Any change, equivalent substitution, and improvement made within the spirit and principle of the present invention shall fall within the protection scope of the claims of the present invention.

What is claimed is:

1. A method for preparing troxerutin ester using whole-cell catalysis, comprising the following steps:
    (1) evenly mixing troxerutin with a mixed organic solvent containing pyridine, then adding an acyl donor, and adding microbial cells as a catalyst and allowing a reaction to produce a troxerutin ester, wherein the reaction is conducted under oscillation; and
    (2) after the reaction is finished, separating and purifying a reaction liquid to obtain the troxerutin ester,
    wherein the mixed organic solvent containing pyridine in the step (1) is a binary mixed solvent composed of the pyridine and one of n-heptane and isooctane,
    wherein the acyl donor in the step (1) is vinyl propionate,
    wherein the microbial cell in the step (1) is *Pseudomonas stutzeri* or *Pseudomonas aeruginosa*.

2. The method according to claim 1, wherein a volume content of the pyridine in the mixed organic solvent ranges from 25% to 90%.

3. The method according to claim 1, wherein a molar ratio of the troxerutin to the acyl donor in the step (1) is 1:5 to 1:40.

4. The method according to claim 1, wherein a mass ratio of the microbial cell to the troxerutin in the step (1) is 2:3 to 8:3.

5. The method according to claim 1, wherein a temperature of the reaction in the step (1) ranges from 20° C. to 55° C.

6. The method according to claim 1, wherein the reaction in the step (1) lasts for 24 hours to 156 hours.

7. The method according to claim 1, wherein the separating and purifying in the step (2) comprises centrifuging the reaction liquid after the reaction to remove the microbial cells, then performing reduced pressure distillation to remove the mixed organic solvent, and separating by column chromatography or thin-layer chromatography to obtain the troxerutin ester; and a chromatography liquid used is ethyl acetate/methanol/water with a volume ratio of 15:3.6:0.5.

\* \* \* \* \*